(12) United States Patent
Chapman et al.

(10) Patent No.: US 8,008,527 B1
(45) Date of Patent: Aug. 30, 2011

(54) OCTAFLUOROPENTAERYTHRITYLTETRAMINE (OCTAFLUORO-PETA) AND PROCESS FOR ITS PREPARATION

(75) Inventors: Robert D. Chapman, Ridgecrest, CA (US); Richard A. Hollins, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 154 days.

(21) Appl. No.: 12/496,962

(22) Filed: Jul. 2, 2009

(51) Int. Cl.
*C07C 291/00* (2006.01)

(52) U.S. Cl. ........................................ 564/121; 564/122

(58) Field of Classification Search .................. 564/121, 564/122
See application file for complete search history.

(56) References Cited

U.S. PATENT DOCUMENTS

| | | |
|---|---|---|
| 5,789,617 A | 8/1998 | Archibald et al. |
| 7,563,889 B1 | 7/2009 | Chapman et al. |
| 7,632,943 B1 | 12/2009 | Chapman et al. |

OTHER PUBLICATIONS

Database CAPLUS on STN, Acc. No. 1961:13138, Gryszkiewicz-Trochimowski et al., Memorial des Poudres (1958), 40, p. 109-112 (abstract).*
Database CAPLUS on STN, Acc. No. 2006:1344188, Fan et al., Journal of Molecular Structure (2006), 801(1-3), p. 55-62 (abstract).*
Chapman, Robert D., N,N-Dihaloamine explosive as harmful agent defeat materials, Nov. 13, 2008, slides 1-10, US.

* cited by examiner

*Primary Examiner* — Brian J Davis
(74) *Attorney, Agent, or Firm* — Charlene A. Haley

(57) ABSTRACT

A composition and method of manufacturing the same. Embodiments of an aspect of the invention relate to the formula $C(CH_2NF_2)_4$ having the name octafluoropentaerythrityltetramine (octafluoro-PETA). In embodiments of another aspect generally relate to a method for manufacturing octafluoropentaerythrityltetramine (octafluoro-PETA) including, basifying pentaerythrityltetramine tetrahydrochloride in an aqueous solution with an aqueous alkali and treating with alkyl chloroformate for producing a tetraalkyl pentaerythrityltetra carbamate, extracting the compound into a nonaqueous solvent suitable for extraction from water and removing the solvent for providing a pure form of tetraethyl pentaerythrityltetracarbamate, bubbling elemental fluorine and/or mixtures of fluorine with an inert gas through tetraalkyl pentaerythrityltetracarbamate in a solvent suitable for direct fluorinations of protected amines until excess fluorine appears, and purifying the resultant octafluoropentaerythrityltetramine.

13 Claims, 1 Drawing Sheet

Figure 1:
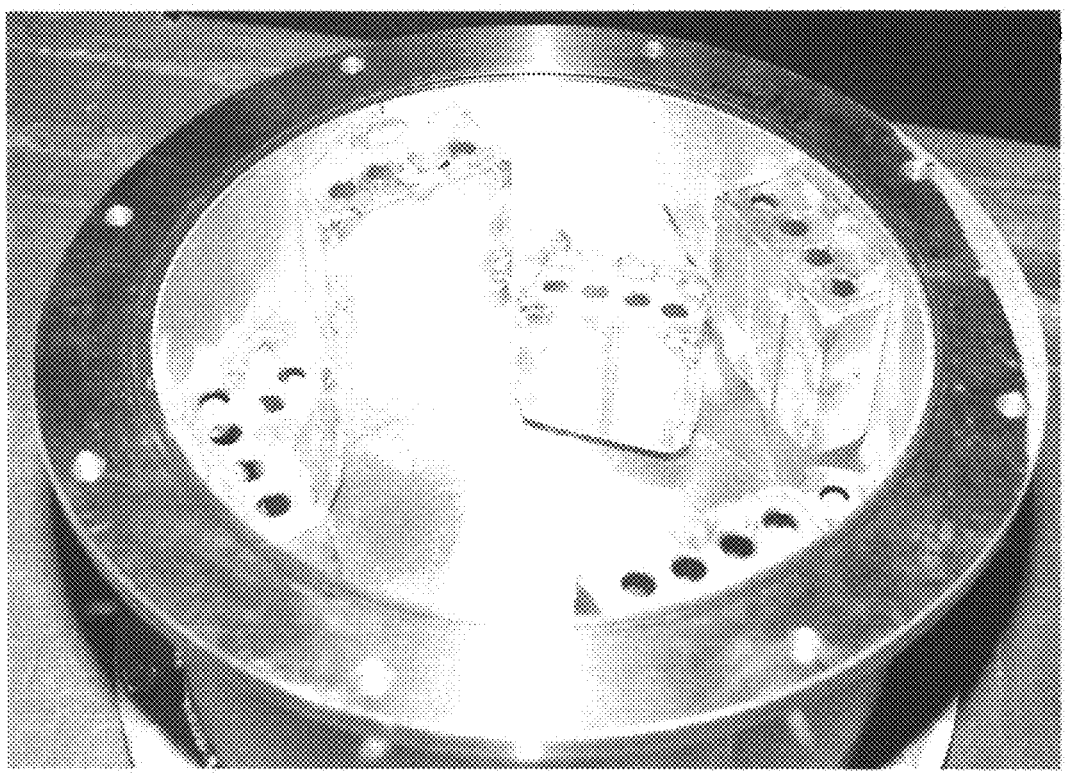

OCTAFLUOROPENTAERYTHRITYLTETRAMINE (OCTAFLUORO-PETA) AND PROCESS FOR ITS PREPARATION

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

Embodiments of the invention relate to biocidal explosive compositions, methods for producing the same, and methods for eradicating harmful chemical and biological agents, more specifically, difluoramine-based explosives that during and/or after detonation produce detonation products that act as efficient biocides upon their exposure.

BACKGROUND OF THE INVENTION

The term "biocide" or "biocidal" refers to a chemical substance capable of killing living organisms, usually in a selective way. Biocides are commonly used in medicine, agriculture, forestry, and in industry where they prevent the fouling of water and oil pipelines. Some substances used as biocides are also employed as anti-fouling agents or disinfectants under other circumstances. The term "biological agent" refers to any living organisms or the materials derived from them (including, but not limited to, bacteria, viruses, fungi, and toxins) that cause disease in or harm to humans that could be used in biological warfare. Harmful biological agents include anthrax (*Bacillus anthracis*) spores. The term "agent" refers to biological agents.

Past agent defeat projects have used hydrogen chloride as a chemical neutralizer, e.g., Lockheed Martin's "Agent Defeat Warhead Device": "These propellants produce gas-phase water and hydrogen chloride that combine to form very reactive hot hydrochloric acid; and as the reactants cool the cooled hydrochloric acid remains in the bunker and may act to continue neutralization of bunker contents for many days . . . . Thus, incendiary agents based on standard composite rocket propellant technology are logical choices for the application described herein." [Jones, J. W. U.S. Pat. No. 6,382,105 (2002)]. It has long been known that HCl has among the poorest bactericidal activities of common acid species. [Paul, T. et al. *Biochemische Zeitschrift* 1911, 29, 202].

Other agent defeat concepts have employed elemental chlorine (a more efficient biocide than HCl) [http://www.globalsecurity.org/military/systems/munitions/adw.htm]. Such formulations so far have produced only low levels of $Cl_2$. One drawback of $Cl_2$ deployment is residual toxic chloro-organics such as chloramines, etc.

In contrast to HCl, hydrogen fluoride (HF) is an efficient antibacterial, antimicrobial biocide: 200 ppm aq. HF destroys *Pseudomonas aeruginosa* and *Saccharomyces diastaticus* in 5 min [Bessems, E.; Ringer, R. GB Patent 1584845 (1981)]; and 1-100 ppm aq. HF sterilizes water lines [Tatsuno, T. et al. U.S. Pat. No. 5,147,605 (1992)].

Novel energetic materials have been sought whose deployment would produce biocidal reaction products following explosive events that destroy a structure or containers involving harmful chemical or biological agents, thus neutralizing the agents post-blast. Based on the attractiveness of hydrogen fluoride as a superior agent defeat by-product—from its known biocidal activity—a class of energetic ingredient that appeared particularly promising for incorporation into explosive formulations for the specific application of agent defeat weapons was the class of energetic difluoramines. One such attractive new difluoramine derivative was 3,3,7,7-tetrakis(difluoramino)octahydro-1,5-dinitro-1,5-diazocine (HNFX), which has been demonstrated to be totally effective (>6 orders of magnitude) in destroying surrogates of anthrax spores [Chapman, R. D. et al. "N,N-Dihaloamine Explosives as Harmful Agent Defeat Materials," DTRA Basic Research Program Technical Review (Springfield, Va.), November 2008; http://www.dtra-basic-research.org/Basic_Research_Program/files/Nov__13__2008/Chapman.pdf]. However, HNFX is prohibitively expensive to produce and deploy.

Thus, there exists a need in the art for such an explosive that is inexpensive, has high biocidal activity during and/or after detonation, and is an easily synthesized, powerful and efficient chemical neutralizer.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

BRIEF DESCRIPTION OF THE DRAWING

FIG. 1 is a prospective view illustrating a detonation testing device, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention generally relate to relates to composition and methods of manufacturing the same. Embodiments of an aspect of the invention relate to the formula $C(CH_2NF_2)_4$ having the name octafluoropentaerythrityltetramine (octafluoro-PETA). In embodiments of another aspect generally relate to a method for manufacturing octafluoropentaerythrityltetramine (octafluoro-PETA) including, basifying pentaerythrityltetramine tetrahydrochloride in an aqueous solution with an aqueous alkali and treating with alkyl chloroformate for producing a tetraalkyl pentaerythrityltetra carbamate, extracting the compound into a nonaqueous solvent suitable for extraction from water and removing the solvent for providing a pure form of tetraethyl pentaerythrityltetracarbamate, bubbling elemental fluorine and/or mixtures of fluorine with an inert gas through tetraalkyl pentaerythrityltetracarbamate in a solvent suitable for direct fluorinations of protected amines until excess fluorine appears, and purifying the resultant octafluoropentaerythrityltetramine.

In embodiments, the aqueous alkali can be sodium hydroxide, the tetraalkyl pentaerythrityltetracarbamate can be a tetraethyl pentaerythrityltetracarbamate compound, the alkyl chloroformate can be ethyl chloroformate, the nonaqueous solvent can be dichloromethane, and the solvent suitable for direct fluorinations of protected amines can be acetonitrile solvent. Another embodiment of this aspect generally relates to a method of producing a biocide, including detonating an N,N-dihaloamine-explosive-based compound to produce a biocidal fluorine derivative. Another embodiment of this aspect includes N-dihaloamine explosive including octafluoropentaerythrityltetramine. Yet another embodiment of this aspect includes a method of producing a biocide including, detonating a N,N-dihaloamine-explosive-based compound to produce biocidal hydrogen fluoride. Still yet another embodiment of this aspect includes a method of producing a biocide including; detonating a N,N-dihaloamine-explosive-based compound to produce biocidal atomic fluorine. When the N,N-dihaloamine explosive is utilized it includes at least octafluoropentaerythrityltetramine. Another aspect of the invention generally relates to a composition, comprising the formula $C(CH_2NCOOR_2)_4$ wherein R is an alkyl group.

A chemical explosive structure that appeared conceptually superior to HNFX was octafluoropentaerythrityltetramine (octafluoro-PETA), $C(CH_2NF_2)_4$, which would produce 58% by weight of biocidal hydrogen fluoride in its detonation products, compared to only about 39% by weight produced by HNFX. Octafluoro-PETA is not enabled by prior art. FIG. 1 illustrates a detonation testing device. The invention of this previously unknown compound is disclosed here, prepared by the synthetic sequence in this diagram.

Octafluoro-PETA (Synthesis)

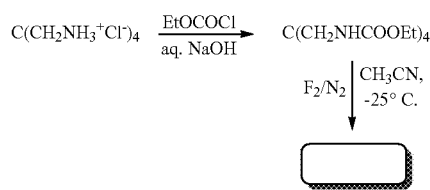

Octafluoro-PETA was successfully synthesized via a new intermediate, tetraethyl pentaerythrityltetracarbamate [$C(CH_2NHCOOCH_2CH_3)_4$], by direct fluorination with elemental fluorine.

Tetraethyl pentaerythrityltetracarbamate was made in one pot in quantitative yield from pentaerythrityltetramine tetrahydrochloride (reported by: Adil, K. et al. *Solid State Sciences* 2004, 6, 1229). A solution of 2.78 g of pentaerythritylamine tetrahydrochloride (10 mmol) in 15 mL of water containing 4.0 g of sodium hydroxide (100 mmol) was cooled in an ice-salt bath, and 6.71 g of ethyl chloroformate (5.89 mL, 60 mmol) was then added slowly over 30 min. After the addition was complete, stirring with cooling was then continued for an additional 1.5 h. The mixture was brought to room temperature, and a solution of 1 mL of ethylchloroformate in 10 mL of methylene chloride was added and stirring continued for an additional 30 minutes. The mixture was extracted with approximately 100 mL of chloroform and the separated organic layer was then dried over anhydrous magnesium sulfate and evaporated on a rotary evaporator giving 3.83 g of white solid (100% yield).

Fluorine (20% in nitrogen) was bubbled through a solution of the tetracarbamate in acetonitrile solvent at −25° C. until excess fluorine appeared in an aqueous iodide trap. The major product was the desired octafluoro-PETA, which was purified chromatographically (silica gel/chloroform). $^1H$ NMR (CDCl$_3$): δ 3.88 (t. 27 Hz). $^{19}F$ NMR (CDCl$_3$): δ 62.13 (t, 27 Hz). $^{13}C$ NMR (CDCl$_3$): δ 38.17 (m), 66.95 (t, 8.8 Hz).

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:
1. A composition, comprising the formula:

$C(CH_2NF_2)_4$ having the name octafluoropentaerythrityltetramine (octafluoro-PETA).

2. A method for manufacturing octafluoropentaerythrityltetramine (octafluoro-PETA), comprising:
basifying pentaerythrityltetramine tetrahydrochloride in an aqueous solution with an aqueous alkali and treating with alkyl chloroformate for producing a tetraalkyl pentaerythrityltetracarbamate;
extracting said compound into a nonaqueous solvent suitable for extraction from water and removing said solvent for providing a pure form of tetraalkyl pentaerythrityltetracarbamate;
bubbling elemental fluorine and/or mixtures of fluorine with an inert gas through said tetraalkyl pentaerythrityltetracarbamate in a solvent suitable for direct fluorinations of protected amines until excess fluorine appears; and
purifying the resultant octafluoropentaerythrityltetramine.

3. The method according to claim 2, wherein said aqueous alkali is sodium hydroxide.

4. The method according to claim 2, wherein said tetraalkyl pentaerythrityltetracarbamate is a tetraethyl pentaerythrityltetracarbamate compound.

5. The method according to claim 2, wherein said alkyl chloroformate is ethyl chloroformate.

6. The method according to claim 2, wherein said nonaqueous solvent is dichloromethane.

7. The method according to claim 2, wherein said solvent suitable for direct fluorinations of protected amines is acetonitrile solvent.

8. A method of producing a biocide, comprising: detonating an N,N-dihaloamine-explosive-based compound to produce a biocidal fluorine derivative.

9. A method for manufacturing octafluoropentaerythrityltetramine (octafluoro-PETA), comprising:
basifying pentaerythrityltetramine tetrahydrochloride in an aqueous solution with an aqueous alkali and treating with alkyl chloroformate for producing a tetraalkyl pentaerythrityltetracarbamate;
extracting said compound into a nonaqueous solvent suitable for extraction from water and removing said solvent for providing a pure form of tetraalkyl pentaerythrityltetracarbamate;
bubbling elemental fluorine and/or mixtures of fluorine with an inert gas through said tetraalkyl pentaerythrityltetracarbamate in a solvent suitable for direct fluorinations of protected amines until excess fluorine appears; and
purifying the resultant octafluoropentaerythrityltetramine, wherein said N,N-dihaloamine explosive comprises octafluoropentaerythrityltetramine.

10. A method of producing a biocide, comprising: detonating a N,N-dihaloamine-explosive-based compound to produce biocidal hydrogen fluoride.

11. A method of producing a biocide, comprising: detonating a N,N-dihaloamine-explosive-based compound to produce biocidal atomic fluorine.

12. A method of producing a biocide, comprising:

basifying pentaerythrityltetramine tetrahydrochloride in an aqueous solution with an aqueous alkali and treating with alkyl chloroformate for producing a tetraalkyl pentaerythrityltetracarbamate;

extracting said compound into a nonaqueous solvent suitable for extraction from water and removing said solvent for providing a pure form of tetraalkyl pentaerythrityltetracarbamate;

bubbling elemental fluorine and/or mixtures of fluorine with an inert gas through said tetraalkyl pentaerythrityltetracarbamate in a solvent suitable for direct fluorinations of protected amines until excess fluorine appears; and purifying the resultant octafluoropentaerythrityltetramine, wherein said N,N-dihaloamine explosive comprises octafluoropentaerythrityltetramine.

13. A composition, comprising the formula:

$C(CH_2NCOOR_2)_4$ wherein R is an alkyl group.

* * * * *